United States Patent [19]

Schimanski et al.

[11] Patent Number: 5,222,186
[45] Date of Patent: Jun. 22, 1993

[54] ELECTRICAL APPARATUS FOR VAPORIZING OF ACTIVE SUBSTANCES

[75] Inventors: Georg Schimanski, Hagen; Horst Hautmann, Neuburg; Jürgen Fischer, Adelschlag, all of Fed. Rep. of Germany

[73] Assignee: Globol GmbH, Neuburg, Fed. Rep. of Germany

[21] Appl. No.: 778,065
[22] PCT Filed: Mar. 13, 1991
[86] PCT No.: PCT/EP91/00473
    § 371 Date: Dec. 6, 1991
    § 102(e) Date: Dec. 6, 1991
[87] PCT Pub. No.: WO91/15249
    PCT Pub. Date: Oct. 17, 1991
[51] Int. Cl.⁵ ............................................... F24F 6/10
[52] U.S. Cl. .................................. 392/395; 392/392; 392/405
[58] Field of Search ............... 392/394, 395, 392, 403, 392/405, 406

[56] References Cited

U.S. PATENT DOCUMENTS 3,431,393  3/1969  Katsuda .
5,038,394  8/1991  Hasegawa ........................... 392/395

FOREIGN PATENT DOCUMENTS 137153   2/1933  Austria ................................ 392/391
0334785  7/1989  European Pat. Off. .
530009  12/1921  France ................................ 392/395
59-62784  4/1984  Japan ................................. 392/395
62-45986  3/1987  Japan ................................. 392/395
1123922  6/1968  United Kingdom .
1123923  9/1968  United Kingdom .

Primary Examiner—Teresa J. Walberg
Attorney, Agent, or Firm—Sixbey, Friedman, Leedom & Ferguson

[57] ABSTRACT

To provide an electrical apparatus for vaporizing active substances, perfumes or the like volatile substances, consisting of a housing having an electrical heating means and a container for liquid to be vaporized connectable to the housing, in the container a wick or the like being mounted by means of which the liquid is supplied to the heating means, and the wick passes through the heating means at a through passage adapted to the wick, the heating means further consisting of a ceramic heating body with electrical heating coil let into said body, said coil having a high functional reliability and long life with simple production, it is proposed that the heating body (2) comprises a recess (8) which extends tangentially to its through passage (5) and which is made rectilinear and into which the heating coil (7) is inserted, and which is filled with potting composition, the electrical leads (9) of the heating coil (7) being led out of the heating body (2) substantially coaxially to the heating coil (7).

15 Claims, 4 Drawing Sheets

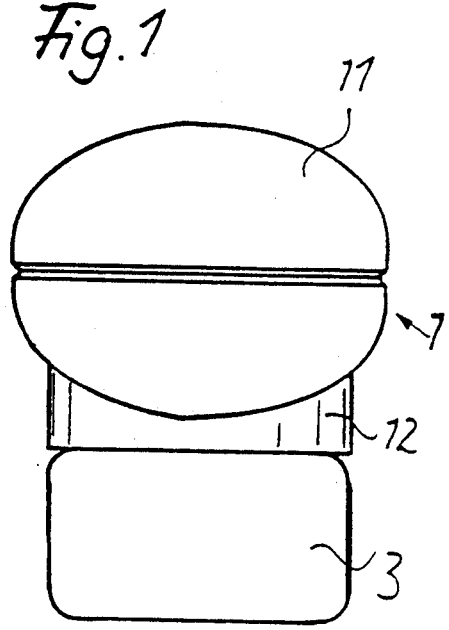
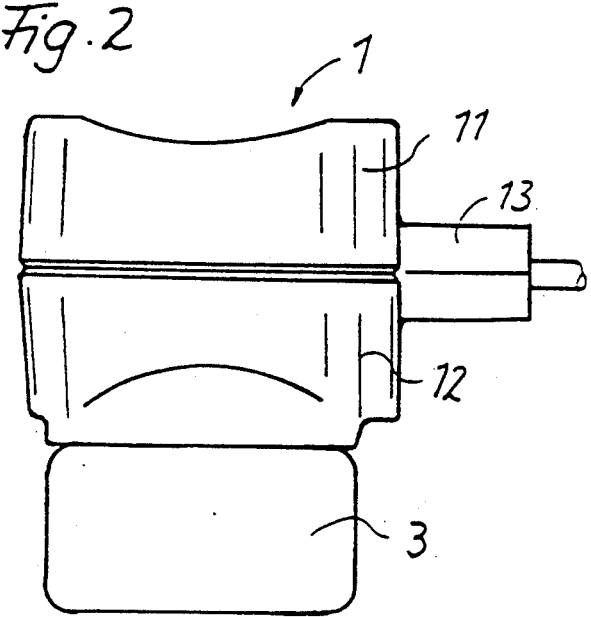
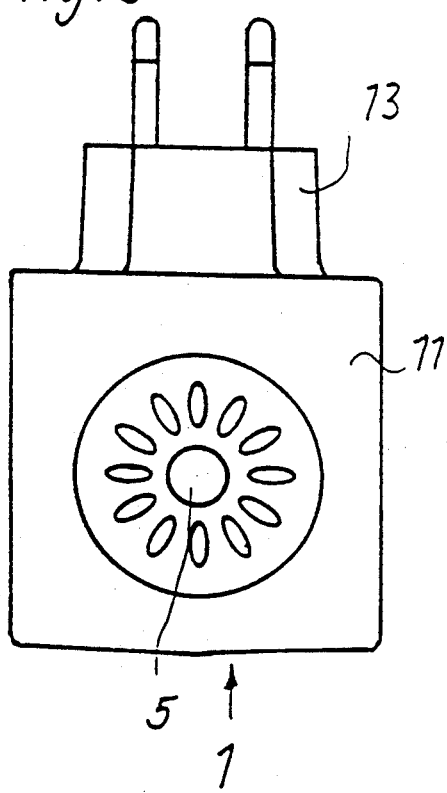
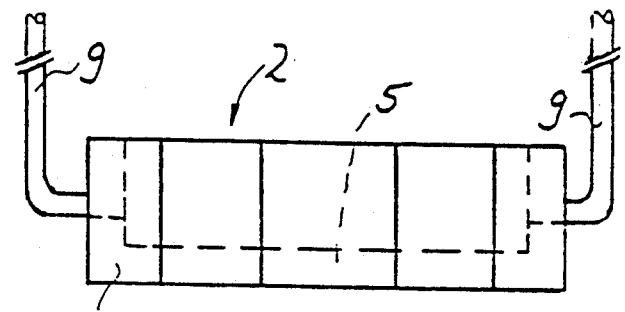
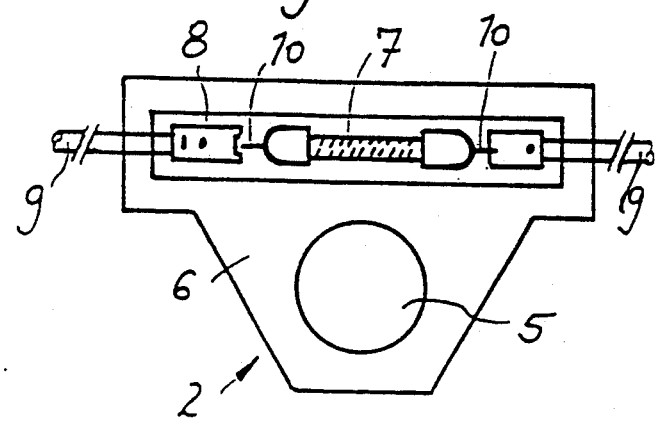

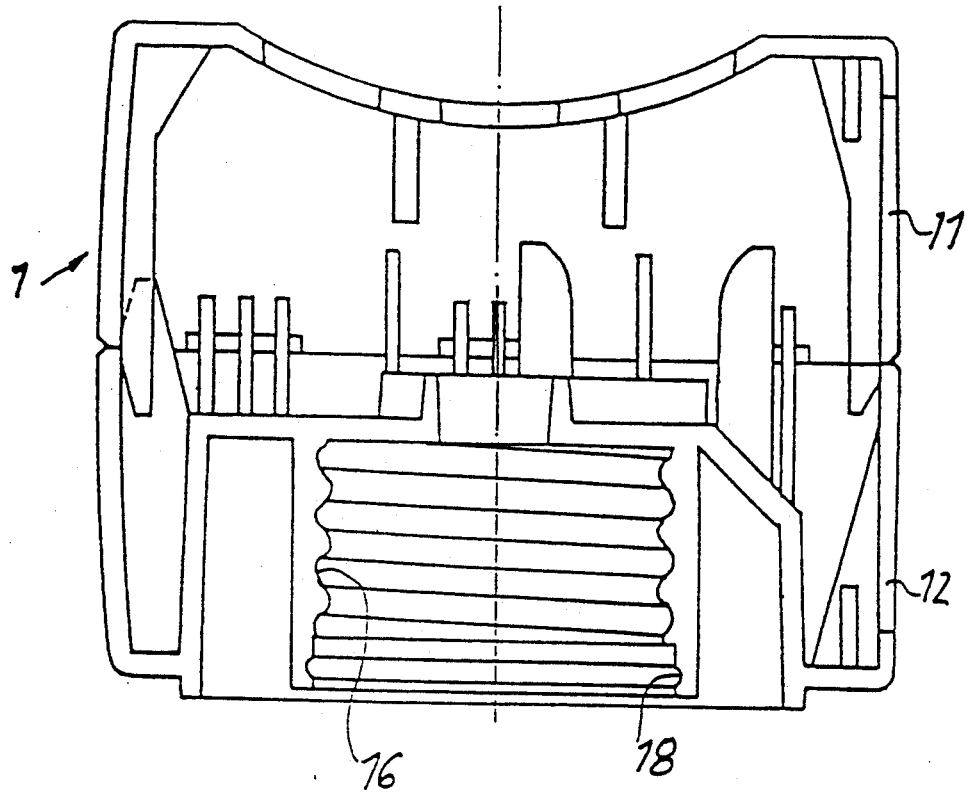
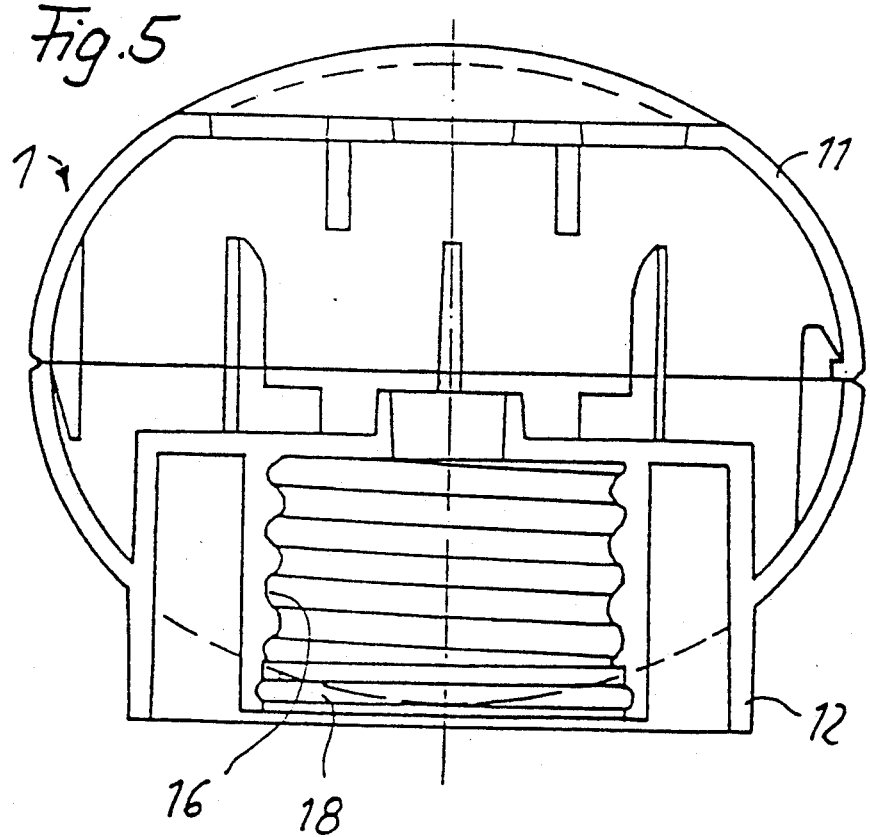

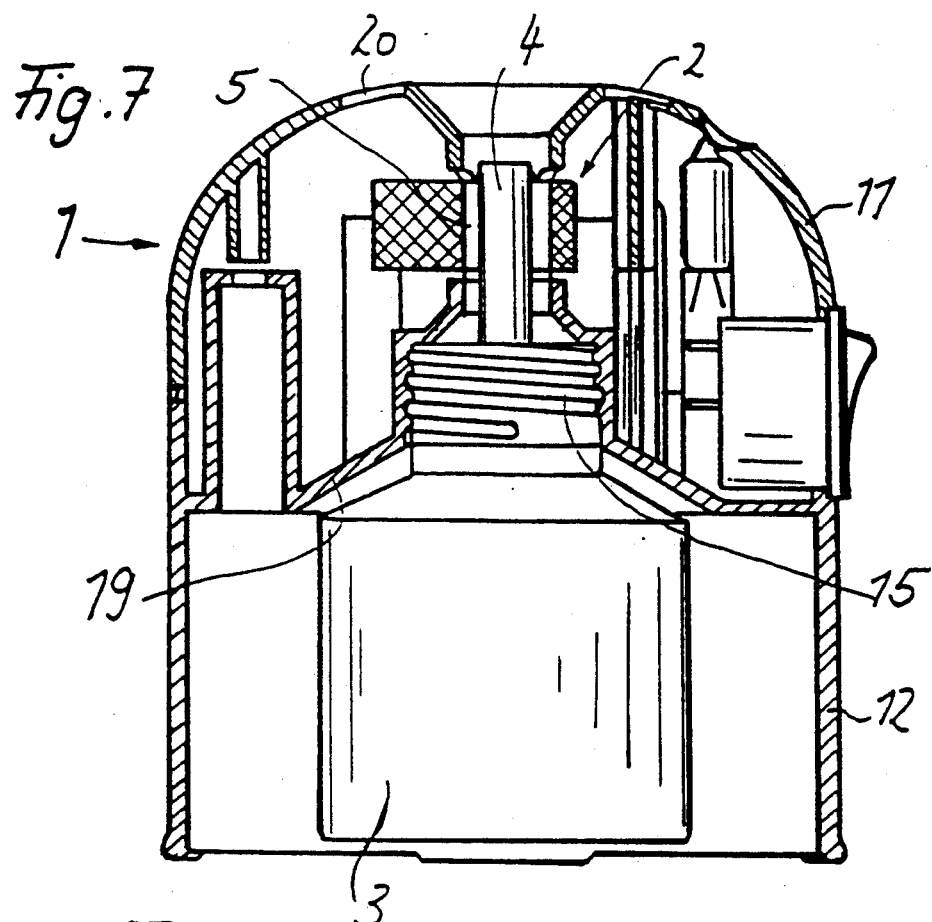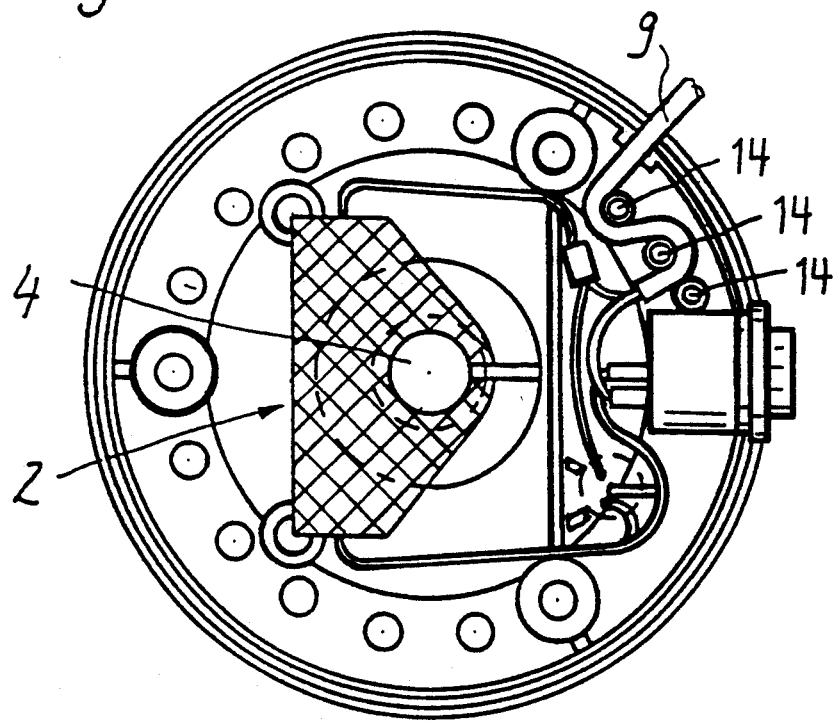

ELECTRICAL APPARATUS FOR VAPORIZING OF ACTIVE SUBSTANCES

The invention relates to an apparatus for vaporizing active substances, perfumes or similar volatile substances, consisting of a housing comprising an electrical heating means and a container for the liquid to be vaporized which is connectable to the housing and in which a wick or the like is mounted by means of which the liquid is supplied to the heating means, and the wick passes through the heating means at a through passage adapted to the wick, the heating means further consisting of a ceramic heating body with an electrical heating coil let into said body.

Such apparatuses are known in the art.

The known apparatuses are disadvantageous in many respects. In particular, the constructional form is very complicated because a great number of individual parts have to be assembled together and these parts are technically complicated to manufacture. A further disadvantage is that in the known apparatuses according to the preamble the heating body is formed as circular disc which has a centre hole serving to receive the wick end. The heating coil is inserted bent into the ceramic heating body, following the shape thereof, and this leads firstly to assembly difficulties and secondly makes a properly located supplying and arrangement of the heating coil in the heating body extremely difficult. Moreover, due to the necessarily provided bending of the heating coil the distance between the individual convolution flights of the heating coil on the inside is relatively very small but on the outside relatively large and this results in an ununiform heating load which is detrimental to the life of the heating coil. Furthermore, in the known apparatuses the wick configuration is disadvantageous because the proper supply of liquid from the container to the heating means is not always ensured, as practical experience has shown.

Proceeding from this prior art, the problem underlying the invention is to provide an apparatus of the type according to the preamble which with simple production has high functional reliability and a long life.

To solve this problem it is proposed that the heating body comprises a recess extending tangentially to its through passage which is made rectilinear and into which the heating coil is inserted and which is filled with potting composition, the electrical leads of the heating coil being led out of the heating body substantially coaxially to the heating coil.

This configuration achieves that the heating body itself is simpler to make than hitherto and in particular also a uniform heat load is obtained after the proper arrangement of the heating coil. The arrangement of the heating coil itself involves no problems at all because said coil can be inserted into the rectilinear recess and finally fixed there by potting or casting composition. It is of course also possible instead of the single arrangement of a heating coil to arrange two heating coils extending for example parallel to each other on either side of the through passage in the surface of the heating body, the latter then having to have two parallel recesses for this purpose. The ceramic composition of the heating body itself effects the heat conduction and thus a uniform distribution within the entire heating body of the heat produced by the heating coil so that the through passage is heated largely uniformly and thus a uniform emission of aromatic substance from the wick end disposed in the through passage can be achieved.

A preferred further development is seen in that the heating body is a substantially triangular flat disc, the through passage is formed extending transversely to the area extent of the disc near one tip thereof and near the edge opposite said tip the recess for the heating coil is arranged.

This configuration is firstly compact and secondly saves material and as a result a more economical configuration is obtained whilst retaining the advantage of assembly and efficiency.

A preferred further development is seen in that the heating coil has a length corresponding substantially to the diameter of the through passage.

In a particularly preferred further development the leads are electrically connected within the recess to the terminal ends of the heating coil, the connection points are covered like the heating coil with potting composition and the insulated leads are led out of the heating body.

This ensures that the electrically uninsulated connecting points are insulated by the potting composition itself so that outside the heating body only insulated leads are disposed.

To achieve uniform supply of liquid from the container to the heating means, it is proposed that the wick consists of a plurality of textile individual filaments which extend parallel to each other in the longitudinal direction of the wick and which are held together and surrounded by a tube-like fabric sheath, the individual filaments projecting beyond the fabric sheath at both wick ends.

This configuration ensures on the one hand an improved and permanent liquid supply from the container to the heating means and on the other hand the tube-like fabric sheath can be served to a greater or lesser extent both at the container-side end of the wick and at the heating-side end of the wick so that a varying degree of opening of the individual filaments of the wick at the two ends is possible.

A further preferred embodiment is seen in that the housing consists of two half shells, one of which forms the housing base with container connection means and the other of which forms the housing top, the heating means being held clamped between the two.

This arrangement facilitates production and assembly and is in addition a configuration having cost advantages.

If the apparatus is constructed as plug-type apparatus it is advantageous if the leads are led to a connector plug mounted for limited relation between the edges of the housing half shells.

In a further development in which the apparatus is used as standing apparatus and consequently a longer connection cable is required for connection to a corresponding socket, it is preferably provided that the leads are surrounded by an insulating sheath, led in zig-zag manner round pins projecting from the housing base to the housing top, and emerge radially from the housing.

By the zig-zag path through the housing pins a tension relief is achieved of the connecting cable (by the insulating sheath surrounding the leads) without additional screw or other securing means being necessary for this purpose.

Furthermore, it is preferably provided that the container is provided at the wick outlet opening with an outer threaded neck which can be screwed into a corresponding threaded recess of the base.

It is particularly preferred that on the neck of the container lying at the rear in the screw-in direction of the thread an encircling ring rib is formed and an annular groove is formed at the front in the threaded recess of the housing, the ring rib engaging in the annular groove when the container is in the screwed-in desired position.

With this construction a detent securing is achieved which ensures that the user can perceivably set the desired end position of the container and housing with respect to each other. When screwing the container into the housing, firstly a rotation is effected within the thread flights until the ring rib reaches the region in which the annular groove is disposed. The ring rib, which preferably projects slightly beyond the thread configuration, then engages lockingly into the correspondingly formed annular groove so that a defined end position is set which additionally forms a certain children's safety lock.

It is of course also possible to provide conventional children-proof safety means for the coupling of container and housing.

A possible variant is seen in that the bottom of the container forms the standing base of the apparatus.

A possibly preferred variant resides in that the side walls of the housing are formed to project beyond the bottom surface of the container.

It is preferred here that when the container is in the screw-in desired position between the container outer wall and the inner wall of the housing base an air gap is formed which opens into corresponding through openings of the housing.

It is of course also advantageous for the side walls of the housing base bearing on the bottom to have in the bottom area recesses for the entry of air, or for the housing itself to have holes or the like in the region of the base as well for the purpose of air supply.

Examples of embodiment of the invention are illustrated in the drawing and will be described in detail hereinafter.

In the drawing

FIG. 1 shows a first embodiment of the apparatus according to the invention in side elevation;

FIG. 2 shows the same embodiment turned through 90°;

FIG. 3 is a view of the apparatus according to FIG. 1 seen from above;

FIG. 4 shows individual parts of the apparatus in the view according to FIG. 2;

FIG. 5 shows the individual parts in the view according to FIG. 1;

FIG. 6 shows a component in the view according to FIG. 1 with the container screwed in;

FIG. 7 illustrates another embodiment in side view, partially sectioned;

FIG. 8 shows the embodiment of FIG. 7 in section seen from above;

FIG. 9 shows a detail in side elevation;

FIG. 10 shows a detail in plan elevation.

Figure 6:
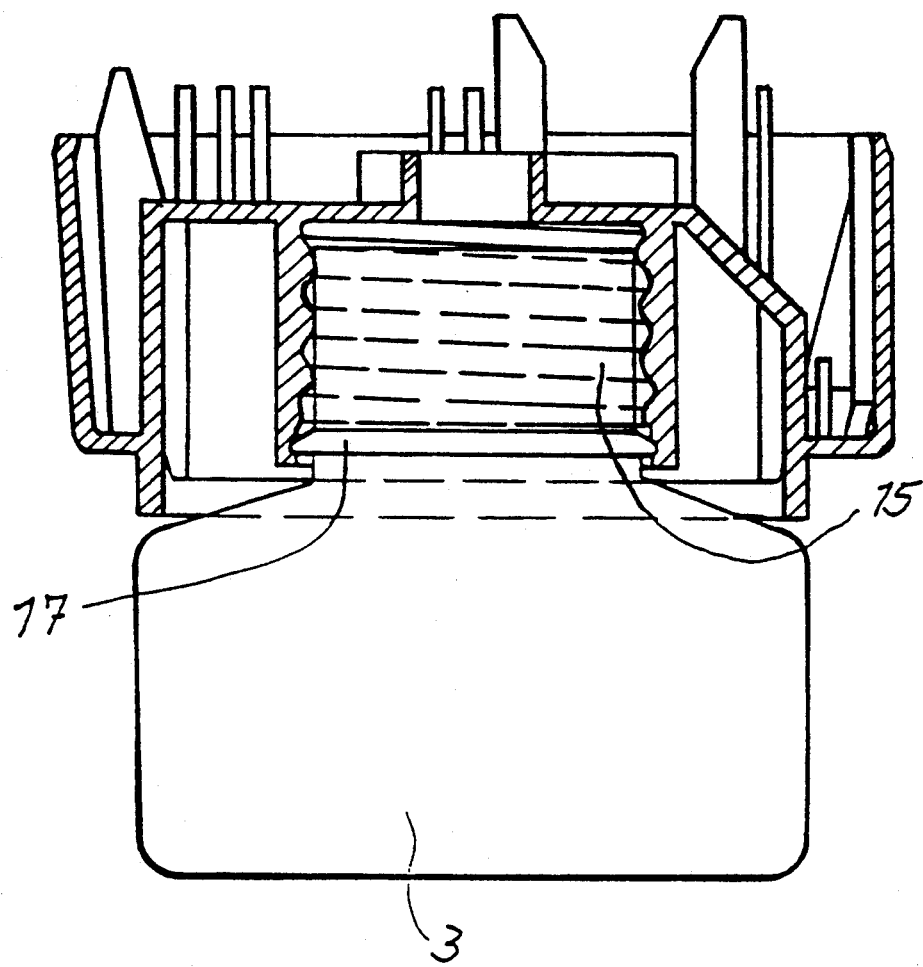

The electrical apparatus for vaporizing active substances, perfumes and the like volatile substances consists essentially of a housing 1 having an electrical heating means 2 and a container 3 for the liquid to be vaporized which is connectable to the housing 1. Mounted in the container 3 is a wick 4 by means of which the liquid is supplied from the container 3 to the heating means 2.

The wick 4 passes through the heating means 2 at a through passage 5 adapted to the wick. The heating means 2 consists of a ceramic heating body 6 with an electrical heating coil 7 let into said body. As apparent in particular from FIG. 10, the heating body 2 comprises a recess 8 which extends tangentially to its through passage 5 and is made rectilinear and into which the heating coil 7 is inserted likewise rectilinearly. When the components are in the desired position the recess 8 is filled with potting composition so that a closed heating body 2 results as is apparent for example from FIG. 8. The electrical leads 9 of the heating coil 7 are led out of the heating body 2 substantially coaxially to the heating coil 7. In a preferred embodiment illustrated in the drawings the heating body 2 is formed by a substantially triangular flat disc, near the one tip of which, which is flattened in the example of embodiment, the through passage is formed extending transversely to the surface longitudinal extent of the disc. Near the edge of the disc opposite said tip the recess 8 for the heating coil 7 is formed. The heating coil 7 has a length substantially corresponding to the diameter of the through passage 5. Within the recess 8 the leads 9 are electrically connected to the terminal ends 10 of the heating coil 7, the connecting points being covered like the heating coil 7 with the potting composition. The insulated connecting conductors or leads 9 are led out of the heating body 2. The configuration of the wick 4 is preferably such that a plurality of textile individual filaments extending parallel to each other in the longitudinal direction of the wick are held together and surrounded by a tube-like fabric sheath, the individual filaments projecting beyond the fabric sheath at both wick ends.

As apparent in particular from FIGS. 4, 5 and 7, the housing 1 consists of two half shells 11, 12, one (12) of which is formed as housing base with container connecting means and the other (11) of which forms the housing top, the heating means 2 being clamped between the two housing parts. The leads 9 in the example of embodiment according to FIGS. 1 to 3 are led to a connector plug 13 held for limited rotational movement between the edges of the housing half shells 11, 12. The connector plug is rotatable so that it can be aligned firstly in the position according to the drawings and secondly in a position turned through 90°.

As apparent in particular from FIG. 8, the leads 9 are surrounded by an insulating sheath and are led round pins 14 projecting from the housing base 12 to the top 11 and emerge radially from the housing 1. Due to the zig-zag shaped guiding via the pins 14 a tension relief of the lead cable is achieved.

As apparent in particular from FIGS. 6 and 7, the container 3 is provided at the wick outlet opening with an externally threaded neck 15 which can be screwed into a corresponding threaded recess 16 of the base 12. In the example of embodiment according to FIGS. 4 to 6, on the neck of the container 3 at the rear in the screw-in direction of the thread 15 an encircling ring rib 17 is provided whilst in the threaded recess 16 of the housing a ring groove 18 is formed at the front. When the parts are in the screwed-in desired position as shown in FIG. 6, the ring rib 17 is lockingly engaged into the annular groove 18. As a result, a perceivable resistance is formed which on the one hand defines the screwed-in desired position and on the other represents a resistance against screwing out (child-proof securing). Optionally, the bottom 3 of the container may be formed as standing surface of the entire apparatus 1. However, in the example of embodiment according to FIG. 7 the side walls of the housing base 12 are made to project beyond the bottom face of the container 3, and by overhangs of the housing side wall edge air supply means are formed. The air supply, which takes place at the bottom at the housing base 12, can be through holes or gaps 19 and 20 in the housing base or top. It is of course possible for the holes or gaps 19, 20 to be arranged in uniform distribution.

The invention is also not restricted to the examples of embodiment but can be varied in many ways within the scope of the disclosure.

All the new single and combination features disclosed in the description and/or drawings are considered essential to the invention.

We claim:

1. Electrical apparatus for vaporizing active substances, perfumes or similar volatile substances, comprising a housing having an electrical heating means and a container for the liquid to be vaporized which is connectable to the housing and in which a wick is mounted by means of which the liquid is supplied to the heating means, and the wick passes through the heating means at a passage adapted to the wick, the heating means further comprising a ceramic heating body with an electrical heating coil let into said body, wherein the heating body comprises a recess extending tangentially to said passage, said recess being rectilinear and into which the heating coil is inserted and which is filled with potting composition.

2. Electrical apparatus according to claim 1 wherein the heating body is a substantially triangular flat disc, the through passage is formed extending transversely to the area extent of the disc near one tip thereof and near the edge opposite said tip the recess for the heating coil is arranged.

3. Electrical apparatus according to claim 1, wherein the heating coil has a length corresponding substantially to the diameter of the passage.

4. Electrical apparatus according to claim 1, wherein the heating body is provided with leads which are electrically connected within the recess to terminal ends of the heating coil, and wherein the connection points are covered with a potting composition.

5. Electrical apparatus according to claim 1, wherein the heating coil is covered with a potting composition, whereas the insulated leads are led out of the heating body.

6. Electrical apparatus according to claim 1, wherein the wick consists of a plurality of textile individual filaments which extends parallel to each other in the longitudinal direction of the wick and which are held together and surrounded by a tube-like fabric sheath, the individual filaments projecting beyond the fabric sheath at both wick ends.

7. Electrical apparatus according to claim 1, wherein the housing consists of two half shells, one of which forms the housing base with container connection means and the other of which forms the housing top, the heating means being held clamped between the two shells.

8. Electrical apparatus according to claim 1, wherein the heating body comprises leads which are led to a connector plug mounted for limited relation between the edges of the housing half shells.

9. Electrical apparatus according to claim 1, wherein the heating body comprises leads which are surrounded by an insulating sheath, led in zig-zag manner round pins projecting from the housing base to the housing top, and emerge radially from the housing.

10. Electrical apparatus according to claim 1, wherein the container is provided at the wick outlet opening with an outer threaded neck which can be screwed into a corresponding threaded recess of the base.

11. Electrical apparatus according to claim 1, wherein the container comprises a neck and wherein on the neck of the container lying at the rear in the screw-in direction of the threaded an encircling ring rib is formed and an annular groove is formed at the front in the threaded recess of the housing, the ring rib engaging in the annular groove when the container is in the screwed-in desired position.

12. Electrical apparatus according to claim 1, wherein the container comprises a bottom which forms the standing base of the apparatus.

13. Electrical apparatus according to claim 1, wherein the housing comprises a base with side walls which are formed to project beyond the bottom surface of the container.

14. Electrical apparatus according to claim 1, wherein the container comprises an outer wall and the housing an inner wall, and wherein the container may be brought into a screw-in desired position between the container outer wall and the inner wall of the housing base an air gap is formed which opens into corresponding through openings of the housing.

15. Electrical apparatus according to claim 1, wherein the heating coil comprises electrical leads which are led out of the heating body substantially coaxially to the heating coil.

* * * * *